(12) United States Patent
Rees et al.

(10) Patent No.: US 8,921,269 B2
(45) Date of Patent: Dec. 30, 2014

(54) COMPOSITION AND SYSTEM FOR TURF MAINTENANCE

(75) Inventors: Richard Rees, Chapel Hill, NC (US); Richard K. Hanrahan, Englewood, NJ (US); Ed Vandenberg, Guelph (CA)

(73) Assignee: Bayer CropScience LP, Research Triangle Park, NC (US)

( * ) Notice: Subject to any disclaimer, the term of this patent is extended or adjusted under 35 U.S.C. 154(b) by 967 days.

(21) Appl. No.: 12/867,152

(22) PCT Filed: Feb. 19, 2009

(86) PCT No.: PCT/US2009/034484
§ 371 (c)(1),
(2), (4) Date: Sep. 9, 2010

(87) PCT Pub. No.: WO2009/126370
PCT Pub. Date: Oct. 15, 2009

(65) Prior Publication Data
US 2013/0203600 A1      Aug. 8, 2013

Related U.S. Application Data

(60) Provisional application No. 61/123,389, filed on Apr. 8, 2008.

(51) Int. Cl.
| | | |
|---|---|---|
| A01N 55/02 | (2006.01) | |
| A01N 57/00 | (2006.01) | |
| A01N 57/20 | (2006.01) | |
| A01N 27/00 | (2006.01) | |
| A01N 37/42 | (2006.01) | |
| A01N 43/54 | (2006.01) | |
| A01N 43/653 | (2006.01) | |
| A01N 43/713 | (2006.01) | |
| A01N 37/36 | (2006.01) | |

(52) U.S. Cl.
CPC ............... *A01N 57/20* (2013.01); *A01N 27/00* (2013.01); *A01N 37/42* (2013.01); *A01N 43/54* (2013.01); *A01N 43/653* (2013.01); *A01N 43/713* (2013.01); *A01N 37/36* (2013.01)

USPC ............... 504/126; 504/127; 504/128

(58) Field of Classification Search
CPC ............... A01N 55/02; A01N 57/00
See application file for complete search history.

(56) References Cited

U.S. PATENT DOCUMENTS

| | | | | |
|---|---|---|---|---|
| 5,336,661 A | * | 8/1994 | Lucas ........................ | 504/126 |
| 6,248,761 B1 | * | 6/2001 | Fujimoto .................. | 514/345 |
| 2006/0276339 A1 | | 12/2006 | Windsor et al. | |
| 2006/0293188 A1 | | 12/2006 | Norton et al. | |
| 2011/0294666 A1 | * | 12/2011 | Cordingley et al. ........ | 504/130 |

FOREIGN PATENT DOCUMENTS

| | | | |
|---|---|---|---|
| DE | 130199 | * | 3/1978 |
| EP | 132900 | * | 2/1984 |
| EP | 0132900 A1 | | 2/1985 |
| JP | 59196801 A | | 11/1984 |
| JP | 3-221576 | | 9/1991 |
| JP | 10276570 A | | 10/1998 |
| JP | 2004524341 A | | 8/2004 |
| WO | 02/076212 A1 | | 10/2002 |
| WO | WO 02076212 | * | 10/2002 |
| WO | 2007/068421 A2 | | 6/2007 |
| WO | WO 2007068421 | * | 6/2007 |

OTHER PUBLICATIONS

Printout of http://www2.siri.org/msds/f2/bzz/bzzsc.html, for ingredients in Rohm and Haas Co.'s Fore.Tm. Fungicide, 62440 (Jul. 24, 1991).*
Office Action of Japanese Patent Application No. 2011-504023 dated Sep. 25, 2013.
International Search Report for PCT/US09/34484, Filed Feb. 19, 2009.

* cited by examiner

*Primary Examiner* — Alton Pryor

(57) ABSTRACT

The present invention provides an agricultural composition comprising a plant growth regulator and a pigment that provides reduced phytotoxicity as compared to an equivalent application of the plant growth regulator alone. The composition can further include a fungicide. A system for turf management as well as methods for enhancing turf are also provided.

23 Claims, No Drawings

COMPOSITION AND SYSTEM FOR TURF MAINTENANCE

CROSS-REFERENCE TO RELATED APPLICATIONS

This application claims the benefit of U.S. Provisional Application No. 61/123,389, filed Apr. 8, 2008.

BACKGROUND OF THE INVENTION

1. Field of the Invention

The present invention includes a composition comprising an agricultural mixture containing at least one pigment. The present invention includes compositions, methods for manufacture, methods for use, and turf maintenance kits.

2. Description of Related Art

Warm season grasses provide lush green carpets and ornamental borders for a wide range of commercial purposes such as lawns, parks, golf courses, ground covers, and sports fields. These grasses thrive well in warm weather climates and during the warm season of cold weather climates. During periods of cold, however, even of short duration, grasses such as Bermuda grass go dormant and turn brown. Further, under dry winter conditions, these grasses not only turn in color, their growth is stunted and they tend to go to seed thus destroying their green carpet or ornamental effect. Natural grasses that remain green during cold weather for the most part do not provide the richness and visual beauty of warm season grasses.

Where warm season grasses are planted for warm weather use, attempts are made to hide the withering and browning effects of cold weather. These include over-seeding warm grasses with cold season and transitional grasses such as Kentucky bluegrass, tall fescue, and perennial ryegrass to provide a green cover during the cold season. Nevertheless, if the temperature goes too low, the desired warm season grass requires replanting in the spring. In some cases a green appearance is maintained during the cold season by using green paint to color brown grass or by spreading green pellets to maintain a green color on the ground. In addition to being high maintenance and costly, these solutions do not provide a suitable alternative for the lushness of a warm season grass turf. Further, such solutions may, in fact, harm the underlying turf.

In these paint compositions, permanent pigments in water and latex based suspensions are applied to turf to mask damage or to artificially color warm season grasses during periods of seasonal dormancy. The products, generally, are permanent green paint. These conventionally-employed pigments and dyes are however intended merely to color lawns at their surfaces, and no physiological effects for plants are observed on their coloring components themselves. In these conventional colorant compositions, emulsions of acrylate ester resins, vinyl acetate resins, ethylene-vinyl acetate resins or the like or emulsions of water-dispersible polymers, such as synthetic rubber latexes, are also used as adhesives for fixing coloring components on turfgrass. Incidentally, an emulsion of a polymer generally cannot form polymer films at temperatures lower than its film-forming temperature, so that a coloring component, especially a pigment cannot be fixed on turf grass outside of a specified temperature range. Further, in order to ensure adequate cover, such compositions are normally applied at lower rates per volume and require multiple application passes in different directions for uniform application. An example of a typical rate for such products is approximately 300-800 L/ha.

SUMMARY OF THE INVENTION

The present invention includes an agricultural composition comprising a plant growth regulator and a pigment, where the composition provides reduced phytotoxicity as compared to an equivalent application of the plant growth regulator alone. In one embodiment the composition further includes a fungicide.

In one embodiment the plant growth regulator is ethephon, trinexapac ethyl, paclobutrazole, flurprimidol or a combination thereof.

In one embodiment the fungicide is fosetyl aluminum, trifloxystrobin, triadimefon, triticonazole, iprodione or a combination thereof.

In one embodiment the pigment is at least one compound that provides absorption of blue UV light or red UV light or both red and blue UV light such as a phthalocyanine compound. More specifically, the phthalocyanine compound is Pigment Blue 16, Vat Blue 29, Pigment Blue 15, Heliogen Green GG, Ingrain Blue 14, Ingrain Blue 5, Ingrain Blue 1, Pigment Green 37, Pigment Green 7, or a combination thereof.

As noted, the composition provides reduced phytotoxicity as compared to an equivalent application of the plant growth regulator alone. In one embodiment, the pigment is present in an amount of between about 1 to about 900 parts by weight of the total composition.

In one embodiment the composition is an aqueous suspension or a wettable powder.

The present invention also includes a method for enhancing turf comprising applying an effective amount of a composition comprising at least one plant growth regulator in combination with a phytoregulating amount of at least one pigment.

In one embodiment a first plant growth regulator is present in an approximate amount of about 1 to about 900 parts by weight of the total composition. In another embodiment a second plant growth regulator is present in an approximate amount of about 1 to about 900 parts by weight of the total composition.

In one embodiment a pigment is present in an approximate amount of about 1 to about 900 parts by weight of the total composition.

In one embodiment the composition is applied in an amount of water from about 300 to about 800 L/ha.

In one embodiment the composition is applied to turf selected from Bluegrass, Bentgrass, Fescue, Ryegrass, Wheatgrass, Beachgrass, Orchardgrass, Timothy, Smooth Brome, Bermudagrass, Zoysiagrass, St. Augustinegrass, Centipedegrass, Carpetgrass, Bahiagrass, Kikuyugrass, Buffalograss, Blue Grama, and Sideoats Grama. More specifically the turf is Bluegrass, Bentgrass, Fescue, or Ryegrass. Most specifically, the turf is Bentgrass.

The present invention also includes a system for turf management comprising at least one seasonal application comprising at least one pigment and at least one plant growth regulator wherein at least one of the plant growth regulators targets growth retardation.

In one embodiment the system further includes an additional seasonal application comprising at least one pigment and two or more plant growth regulators wherein at least one of the plant growth regulators targets seed head reduction and at least one of the plant growth regulators targets growth retardation.

In one embodiment the system further includes an additional seasonal application comprising at least one fungicide; at least one pigment; and two or more plant growth regulators wherein at least one of the plant growth regulators targets seed head reduction and at least one of the plant growth regulators targets growth retardation.

In one embodiment the system for turf management includes: (1) a first seasonal application comprising at least one fungicide; at least one pigment; and two or more plant growth regulators wherein at least one of the plant growth regulators targets seed head reduction and at least one of the plant growth regulators targets growth retardation; (2) a second seasonal application comprising at least one pigment; and two or more plant growth regulators wherein at least one of the plant growth regulators targets seed head reduction and at least one of the plant growth regulators targets growth retardation; and (3) a third ore more seasonal applications comprising at least one pigment; and at least one plant growth regulator wherein at least one of the plant growth regulators targets growth retardation. More specifically the first seasonal application is applied when average daily temperatures are about 30° F. to about 80° F.; the second seasonal application is applied when average daily temperatures are about 55° F. to about 95° F.; and the third or more seasonal applications are applied when average daily temperatures are about 30° F. to about 80° F.

DETAILED DESCRIPTION OF THE INVENTION AND PREFERRED EMBODIMENTS

The following definitions are meant to clarify, but not limit, the terms defined. If a particular term used herein is not specifically defined, such term should not be considered indefinite. Rather, terms are used within their accepted meanings.

As used herein, the phrase "plant growth regulator" includes chemicals that are designed to affect plant growth, development, or both. They are applied for specific purposes to affect specific plant responses. Although there is much scientific information on using plant growth regulators, due to the nature of agricultural maintenance, plant growth regulation is not a predictable science. As used herein, the phrase "plant growth regulator" includes products designed to reduce or retard the growth rate of the plant, improve its color and general condition, increase plant branching for enhanced cutting production, or enhance flower initiation or synchronize flowering. As used herein the phrase "plant growth regulator" includes a turf growth regulator.

The phrase "plant growth regulator" includes: antiauxins, such as clofibric acid or 2,3,5-tri-iodobenzoic acid; auxins, such as 4-CPA (4-chlorophenoxyacetic acid), 2,4-D ((2,4-dichlorophenoxy)acetic acid), 2,4-DB (4-(2,4-dichlorophenoxy)butyric acid), 2,4-DEP (tris[2-(2,4-dichlorophenoxy)ethyl]phosphate), dichlorprop ((RS)-2-(2,4-dichlorophenoxy)propionic acid), fenoprop ((RS)-2-(2,4,5-trichlorophenoxy)propionic acid), IAA (indol-3-ylacetic acid or β-indoleacetic acid), IBA (4-indol-3-ylbutyric acid), naphthaleneacetamide, α-naphthaleneacetic acid, 1-naphthol, naphthoxyacetic acid, potassium naphthenate, sodium naphthenate, or 2,4,5-T ((2,4,5-trichlorophenoxy)acetic acid); cytokinins, such as 2iP ($N^6$-(3-methylbut-2-enyl)adenine or N-(3-methylbut-2-enyl)-1H-purin-6-amine), benzyladenine, kinetin, or zeatin; defoliants such as calcium cyanamide, dimethipin, endothal, ethephon, merphos, metoxuron, pentachlorophenol, thidiazuron, or tribufos; ethylene inhibitors, such as aviglycine or 1-methylcyclopropene; ethylene releasers such as ACC (1-aminocyclopropanecarboxylic acid), etacelasil, ethephon, or glyoxime; gibberellins such as gibberellins, gibberellin inhibitors such as trinexapac-ethyl, or gibberellic acid; growth inhibitors such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, or 2,3,5-tri-iodobenzoic acid; morphactins such as chlorfluren, chlorflurenol, dichlorflurenol, or flurenol; growth retardants such as chlormequat, daminozide, flurprimidol, mefluidide, paclobutrazol, tetcyclacis, or uniconazole; growth stimulators such as brassinolide, forchlorfenuron, or hymexazol; and further includes a variety of unclassified plant growth regulators such as benzofluor, buminafos, carvone, ciobutide, clofencet, cloxyfonac, cyanamide, cyclanilide, cycloheximide, cyprosulfamide, epocholeone, ethychlozate, ethylene, fenridazon, heptopargil, holosulf, inabenfide, karetazan, lead arsenate, methasulfocarb, prohexadione, pydanon, sintofen, triapenthenol, or trinexapac.

In one embodiment, the present invention includes at least one plant growth regulator that retards growth. Plant growth regulators designed to retard growth include, but are not limited to, gibberellins, gibberellin inhibitors such as trinexapac-ethyl, gibberellic acid, abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, 2,3,5-tri-iodobenzoic acid, chlorfluren, chlorflurenol, dichlorflurenol, flurenol, chlormequat, daminozide, flurprimidol, mefluidide, paclobutrazol, tetcyclacis, or uniconazole.

In one embodiment, the present invention includes at least one plant growth regulator that reduces seed head reduction. Plant growth regulators desginied to reduce seed head production work through systemic action and include, but are not limited to, calcium cyanamide, dimethipin, endothal, merphos, metoxuron, pentachlorophenol, thidiazuron, tribufos, aviglycine, 1-methylcyclopropene, ACC, etacelasil, ethephon, or glyoxime.

In one embodiment, the composition of the present invention includes at least two plant growth regulators, where at least one plant growth regulator targets growth retardation such as trinexapac-ethyl, and at least one other plant growth regulator targets seed head reduction such as ethephon.

As used herein, the term "pigment" includes any pigment acceptable for agricultural use. For example, the term "pigment" includes suitable benzoporphyrins such as phthalocyanine dyes. In a preferred embodiment, the agricultural composition comprises at least one pigment that provides absorption of blue UV light or red UV light or both blue and red UV light. Suitable phthalocyanine dyes may be metal-free phthalocyanines, or metal phthalocyanines. The metal forming the metal phthalocyanines may be selected from alkali metals, alkali earth metals, and transition metals. In one embodiment, the metal is a transition metal. Examples of suitable metals include but are not limited to, lithium, sodium, potassium, rubidium and cesium from the alkali metal family; berillium, magnesium, calcium, strontium, barium, and radium from the alkali earth metal family; and copper, silver, gold, zinc, cadmium, mercury, scandium, yittrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nichel, palladium, and platinum from the transition metal family. In one embodiment, the present invention includes at least one copper, nickel, cobalt, iron, or zinc phthalocyanine dye.

Phthalocyanine dyes which are useful in the methods of the present invention include substituted and unsubstantiated dyes. Suitable substituted phthalocyanine dyes may be metal-tree phthalocyanines, or metal phthalocyanines, and may be substituted from 1 to 4 times on each isoindole group independently. Examples of suitable substituents for the isoindole groups of phthalocyanine dyes include but are not limited to, halogens, substituted or unsubstituted, saturated or unsaturated, linear, branched or cyclic alkyl, alkoxy, alkylamino, alkylthio, onium, sulphonium, sulphate, and carboxylate. Suitable phthalocyanine dyes are commercially available and include but are not limited to Pigment Blue 16, Vat Blue 29. Pigment Blue 15, Heliogen Green GG, Ingrain Blue 14, Ingrain Blue 5, Ingrain Blue 1, Pigment Green 37, and Pigment Green 7. In one embodiment, the phthalocyanine dye is Pigment Blue 15. In another embodiment, the phthalocyanine dye is any phthalocyanine dye other than Pigment Blue 15.

Thus, in one embodiment the pigment is a phthalocyanine compound. More specifically, the phthalocyanine compound is Pigment Blue 16, Vat Blue 29, Pigment Blue 15, Heliogen Green GG, Ingrain Blue 14, Ingrain Blue 5, Ingrain Blue 1, Pigment Green 37, Pigment Green 7, or a combination thereof.

As used herein, the term "phytotoxicity" includes any compound, composition, or agent that is deleterious to plant health. The term implies being poisonous to plants. Phytotoxicity is a term used to describe the toxic effect of a compound on plant growth.

As used herein, the term "phytoregulation" includes any compound, composition, or agent that controls phytotoxicity of a plant. As one example, as herein defined at least one growth regulator may impart certain phytotoxic effects such as reducing the oxidative process, scalping, or bronzing. The phytotoxic effects include any stress borne through the chemotherapeutic effect of the plant growth regulator. Thus, as used herein, the term "photoregulation" imparts a synergistic effect provided by the at least one pigment used in the composition of the present invention. As discussed in further detail below, the admixing of a pigment portion to a plant growth regulator provides a safening effect, namely reduction in the phytotoxicity of the plant growth regulator. The use of a composition of the present invention is believed to improve health of the plant, which herein includes turf, such as grasses and dicots.

As noted, the composition provides reduced phytotoxicity as compared to an equivalent application of the plant growth regulator alone. In one embodiment, the pigment is present in an amount of between about 1 to about 900 parts by weight of total composition.

In one embodiment a first plant growth regulator, such as trinexapac ethyl, is present in an approximate amount of about 1 to about 900 parts by weight of the total composition.

In another embodiment a second plant growth regulator, such as ethephon, is present in an approximate amount of about 1 to about 900 parts by weight of the total composition.

The compositions of the present invention may be used for any agricultural application. In one embodiment, the present invention is useful for turf, such as grass. In one embodiment, the present invention is useful for turf for athletic purposes, such as golf courses, sports' fields and pitches, and other grounds.

The present invention can be practiced with all turfgrasses, including cool season turfgrasses and warm season turfgrasses. Examples of cool season turfgrasses are Bluegrasses (*Poa* L.), such as Kentucky Bluegrass (*Poa pratensis* L.), Rough Bluegrass (*Poa trivialis* L.), Canada Bluegrass (*Poa compressa* L.), Annual Bluegrass (*Poa annua* L.), Upland Bluegrass (*Poa glaucantha* Gaudin), Wood Bluegrass (*Poa nemoralis* L.). and Bulbous Bluegrass (*Poa bulbosa* L.); the Bentgrasses and Redtop (*Agrostis* L.), such as Creeping Bentgrass (*Agrostis palustris* Huds.), Colonial Bentgrass (*Agrostis tenius* Sibth.), Velvet Bentgrass (*Agrostis canina* L.), South German Mixed Bentgrass (*Agrostis* L.), and Redtop (*Agrostis alba* L.); the Fescues (*Festuca* L.), such as Red Fescue (*Festuca rubra* L.), Chewings Fescue (*Festuca rubra* var. commutata Gaud.), Sheep Fescue (*Festuca ovina* L.), Hard Fescue (*Festuca ovina* var. duriuscula L. Koch), Hair Fescue (*Festuca capillata* Lam.), Tall Fescue (*Festuca arundinacea* Schreb.), Meadow Fescue (*Festuca elanor* L.); the Ryegrasses (*Lolium* L.), such as Perennial Ryegrass (*Lollium perenne* L.), Italian Ryegrass (*Lolium multiflorum* Lam.); the Wheatgrasses (*Agropyron* Gaertn.), such as Fairway Wheatgrass (*Agropyron cristatum* (L.) Gaertn.), Western Wheatgrass (*Agropyron smithii* Rydb.). Other cool season turfgrasses include Beachgrass (*Ammophila* Host.), Smooth Brome (*Bromus inermis* Leyss.), Timothy (*Phleum* L.). Orchardgrass (*Dactylis glomerata* L.), Crested Dog's-Tail (*Cynosurus cristatus* L.). Examples of warm season turfgrasses are the Bermudagrasses (*Cynodon* L. C. Rich), Zoysiagrasses (*Zoysia* Willd.), St. Augustinegrass (*Stenotaphrum secundatum* (Wait.) Kuntze), Centipedegrass (*Eremochioa ophiuroides* (Munro.) Hack.), Carpetgrass (*Axonopus* Beauv.), Bahiagrass (*Paspalum notalum* Flugge.), Kikuyugrass (*Pennisetum clandestinum* Hochst. ex Chiov.), Buffalograss (*Buchloe dactyloides* (Nutt.) Engelm.), Blue Grama (*Bouteloua gracilis* (H.B.K.) Lag. ex Steud.), and Sideoats Grama (*Bouteloua curtipendula* (Michx. Torr.).

In one embodiment the composition may be applied to turf selected from Bluegrass, Bentgrass, Fescue, Ryegrass, Wheatgrass, Beachgrass, Orchardgrass, Timothy, Smooth Brome, Bermudagrass, Zoysiagrass, St. Augustinegrass, Centipedegrass, Carpetgrass, Bahiagrass, Kikuyugrass, Buffalograss, Blue Grama, and Sideoats Grama. More specifically the turf is Bluegrass, Bentgrass, Fescue, or Ryegrass. Most specifically, the turf is Bentgrass.

Thus, the present invention includes an agricultural composition comprising a plant growth regulator and a pigment, where the composition provides reduced phytotoxicity as compared to an equivalent application of the plant growth regulator alone. In one embodiment the composition further includes a fungicide.

As used herein, the term "fungicide" includes chemical compounds used to prevent the spread of fungi or plants in gardens and crops, which can cause serious damage resulting in loss of yield and thus profit. Though oomycetes are not fungi, they use the same mechanisms to infect plants and therefore in phytopathology chemicals used to control oomycetes are also referred to as fungicides. Fungicides are also used to fight fungal infections.

Fungicides can either be contact or systemic. A contact fungicide kills fungi when sprayed on its surface; a systemic fungicide has to be absorbed by the plant. As a non-limiting example, for turf applications, one class of fungicides targets crown and root rot, otherwise known as blight, in turfgrass. Crown and root rot, which cause a decline in turfgrass quality during hot, wet weather, is a disease complex believed to be caused by *Pythium* and *Rhizoctonia* species in combination with environmental and management stresses.

The fungicides of the present invention include products such as benzimidazoles, dicarboximides, anilides, phenylpyrroles, polyoxins, Qol/strobilurins, sterol inhibitors (DMIs), and contact/protectant fungicides. The present invention may include at least one of azoxystrobin, basic salts or hydroxides of copper, benomyl, boscalid, captan, captafol, chloroneb, chlorothalonil, etridiazole, fenarimol, fludioxonil, flutolanil, folpel, fosetyl aluminum, iprodione, mancozeb, maneb, mefenoxam, myclobutanil, PCNB (pentochloronitrobenzene), phosphonates, polyoxin D zinc, potassium carbonate, propamocarb, propiconazole, pyraclostrobin, sulfur, thiophanate-methyl, thiram, triadimefon, including triadimefon in combination with metalaxyl, trifloxystrobin, and vinclozolin. In one embodiment the fungicide is fosetyl aluminum.

As individual fungicides control different diseases and conditions, a combination of such products may provide the desired effect, including either to complete the range of activity of the compounds, to increase persistence, or to reduce fungicidal resistance.

The composition of the invention may also include other fungicidal, anti-mildew phosphorus derivatives, especially 2-hydroxy-1,3,2-dioxaphospholanes and β-hydroxy ethyl phosphates.

For their practical application, the active ingredients in the phytoregulating combinations are used as part of a formulated product which contains a support or a surfactant in addition to the active material according to the invention.

In the context of the invention, a support is an organic or mineral, natural or synthetic material with which the active material is associated to facilitate its application to plants, seeds or soil, or its transportation or handling. The support can be solid, such as clays, natural or synthetic silicates, resins, waxes, solid fertilizers, or fluid, such as water, alcohols, ketones, petroleum fractions. chlorinated hydrocarbons, liquefied gases.

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solution, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of at least one stabilizer or other additives, such as penetration agents, adhesives, anti-lumping agents, colorants, and the like.

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency.

The compositions according to the invention can contain other ingredients, for example protective colloids, adhesives or thickeners, thixotropic agents, stabilizers or sequestrants, as well as other active materials known to have pesticidal properties, especially acaricides or insecticides.

The active materials are, in general, applied to turfgrass either together or separately by spraying a liquid formulation (e.g., an aqueous formulation, including emulsions, or an oil-based formulation) thereof on the turfgrass. The composition comprising at least one plant growth regulator and at least one pigment is typically applied in an amount of from about 0.01 to about 2 kg per hectare, more preferably in an amount of from about 0.05 to about 15 kg per hectare, and still more preferably in an amount of from about 0.1 to about 0.8 kg per hectare, In one embodiment the composition is applied in an amount of water from about 300 to about 800 L/ha.

The present invention also includes a system for turf management comprising at least one seasonal application comprising at least one pigment and at least one plant growth regulator wherein at least one of the plant growth regulators targets growth retardation.

As used herein, the phrase "seasonal application" is used to identify a span of time associated with a growing season. As the Northern and Southern Hemispheres experience different seasons, a term to identify the temperate seasons such as "Spring," "Autumn," or "Fall" may be open to different interpretation depending on geographical location. Further, tropical climates often experience seasons in terms of wet and dry. Thus, the phrase "seasonal application" is herein used, therefore, to associated objective criteria with such seasons regardless of the moniker used.

Thus, one season, referred to as Spring provides the season between winter and summer, when most plants begin to grow, and usually thought of in the Northern hemisphere as consisting of the months from March to May inclusive, and in the Southern hemisphere as September to November. The season as a daily average temperature ranging from about 30° F. to about 80° F.

Another season, referred to as Autumn marks the transition from summer into winter. In the Northern hemisphere, the start of autumn is generally considered to be around September, and in the Southern hemisphere, its beginning is considered to be around March. There exists however different definitions of autumn, some of which are based on the months of the year while others are based on the equinox and solstice. The season as a daily average temperature ranging from about 30° F. to about 85° F.

Summer is the whole months of December, January, and February in the Southern Hemisphere, and the whole months of June, July, and August in the Northern Hemisphere. This meteorological definition of summer also aligns with commonly viewed notion of summer as the season with the longest and warmest days of the year, in which the daylight predominates, through varying degrees. The use of astronomical beginning of the seasons means that spring and summer have an almost equal pattern of the length of the days, with spring lengthening from the equinox to the solstice and summer shortening from the solstice to the equinox, while meteorological summer encompasses the build up to the longest day and decline thereafter, so that summer has many more hours of daylight than Spring. The Summer season as a daily average temperature ranging from about 55° F. to about 95° F.

Winter begins on the winter solstice and ends on the vernal equinox. Calculated meteorologically, winter begins and ends earlier, typically at the start of the month with the equinox or solstice, and is the season with the shortest days and the lowest temperatures. Winter generally has cold weather and, especially in the higher latitudes or altitudes, snow and ice. The coldest average temperatures of the season are typically experienced in January in the Northern Hemisphere and in July in the Southern Hemisphere. The season as a daily average temperature ranging from about 32° F. to about −35° F.

In one embodiment the system further includes an additional seasonal application comprising at least one pigment and two or more plant growth regulators wherein at least one of the plant growth regulators targets seed head reduction and at least one of the plant growth regulators targets growth retardation.

In one embodiment the system further includes an additional seasonal application comprising at least one fungicide; at least one pigment; and two or more plant growth regulators wherein at least one of the plant growth regulators targets seed head reduction and at least one of the plant growth regulators targets growth retardation.

In one embodiment the system for turf management includes: (1) a first seasonal application comprising at least one fungicide; at least one pigment; and two or more plant growth regulators wherein at least one of the plant growth regulators targets seed head reduction and at least one of the plant growth regulators targets growth retardation; (2) a second seasonal application comprising at least one pigment; and two or more plant growth regulators wherein at least one of the plant growth regulators targets seed head reduction and at least one of the plant growth regulators targets growth retardation; and (3) a third seasonal application comprising at least one pigment; and at least one plant growth regulator wherein at least one of the plant growth regulators targets growth retardation. More specifically the first seasonal application is applied when average daily temperatures about 30° F. to about 80° F.; the second seasonal application is applied when average daily temperatures are about 55° F. to about 95° F.; and the third or more seasonal applications are applied when average daily temperatures are about 30° F. to about 85° F.

The scope of the present invention includes combinations of embodiments.

The following examples are provided to illustrate the present invention, and should not be construed as limiting thereof.

EXAMPLE 1

Experiments were conducted to determine if fosetyl-Al turf fungicide sold under the trademark ALIETTE SIGNATURE and available from Bayer CropScience LP of Research Triangle Park, N.C. applied 3 times (3 week interval at 200 g/100 m$^2$, 120 g/100 m$^2$, 120 g/100m$^2$) combined with ethephon sold under the trademark PROXY available from Bayer CropScience of Research Triangle Park, N.C. and trinexapac-ethyl sold under the trademark PRIMO and available from Syngenta Crop Protection Inc. of Greensboro, N.C. (applied twice 3-4 weeks apart) provided improved putting surface quality, overall turfgrass quality and seed head suppression of Poa annua in an early season spray program for preventative cool season pythium and anthracnose control. In the present example, the ALIETTE SIGNATURE contained solid copper phthalocynanine green #7 sold under the trademark SUNFAST, available from Sun Chemical Corporation of Cincinnati, Ohio. Two trials were conducted on two golf courses at different locations (i.e., Location One and Location Two) in Ontario, Canada. Both locations employed established Poa/bentgrass greens. At both locations, the trials were set up on a practice putting green as a non-replicated strip trial with four treatments. The putting green was an established push up Poa annua green with some bentgrass. All applications were made with a commercial golf course sprayer.

Trial Location One

At Location One, the early spring treatment program was conducted as summarized in Table 1.

TABLE 1

| Treatment | Amount | Date |
|---|---|---|
| ALIETTE SIGNATURE | 200 g/100 m$^2$ | 15-April |
| PROXY | 159 ml/100 m$^2$ | 20-April |
| PRIMO | 4 ml/100 m$^2$ | 20-April |
| ALIETTE SIGNATURE | 120 g/100 m$^2$ | 8-May |
| PROXY | 159 ml/100 m$^2$ | 10-May |
| PRIMO | 4 ml/100 m$^2$ | 10-May |
| ALIETTE SIGNATURE | 120 g/100 m$^2$ | 10-June |

In addition to the above spray treatments set forth in Table 1, the cover sprays summarized in Table 2 were applied to the entire trial including the untreated control.

TABLE 2

| Treatment | Date |
|---|---|
| PRIMO and all-purpose fertilizer sold under the trademark NUTRA GREEN available from Grigg Bros. of Albion, ID (product 5-10-5) | 11-April |
| NUTRA GREEN | 19-April |
| 21-0-0 (1/8 pound N/1000) | 27-April |
| PRIMO and a combination of plant health supplements sold under the trademarks GARY'S GREEN P-K PLUS, and ULTRAPLEX all available from Grigg Bros. of Albion, ID. | 2-May |
| Insecticide sold under the trademark MERIT and available from Bayer CropScience LP of Research Triangle Park, NC (watered in for ataenius and weevil-forsythia half green/half gold) | 12-May |
| Granular Epsom Salts (heptahydrate, MgSO$_4$•7H$_2$O) | 16-May |
| Trifloxystrobin fungicide sold under the trademark COMPASS and available from Bayer CropScience LP of Research Triangle Park, NC (for treatment of leaf spot and fusarium) | 19-May |
| 0-0-10 (granular Gypsum) and 0-0-46 (2 pounds K/1000) | 24-May |
| Fungicide sold under the trademark HERITAGE available from Syngenta Crop Protection Inc. of Greensboro, NC (watered in for summer patch) | 26-May |
| PRIMO and a combination of plant health supplements sold under the trademarks GARY'S GREEN, P-K PLUS, and ULTRAPLEX | 4-June |
| PRIMO and a combination of plant health supplements sold under the trademarks GARY'S GREEN, P-K PLUS, and ULTRAPLEX | 20-June |

A root core analysis was conducted for each type of treatment. On the 27th day of June, the top three inches of ten samples were collected and separated from the bottom region of each sample. Both the top and bottom samples were washed using specialized root cleaning procedures. Fresh weights and dry weights of each sample were recorded and compared (% increase in weight) to those sample treated with PRIMO only. The results are summarized in Table 3. The root core analysis of the treatments in this non-replicated study taken 17 days after the last ALIETTE SIGNATURE application date showed unexpected increases in fresh and dry root weights in the combination ALIETTE SIGNATURE/PROXY/PRIMO treatment (171% increase of dry weight) compared to the untreated control which only received two applications of PRIMO only. The PROXY/PRIMO program showed a 125% increase in dry weight of roots while the ALIETTE SIGNATURE only program showed no increase in dry weights compared to the untreated control.

TABLE 3

| Treatment | Fresh Weight (top) | Increase (%) | Fresh Weight (bottom) | Increase (%) | Dry Weight (top) | Increase (%) | Dry Weight (bottom) | Increase (%) |
|---|---|---|---|---|---|---|---|---|
| PRIMO Only (untreated control) | 5.3836 | — | 0.0387 | — | 1.5171 | — | 0.0083 | — |
| ALIETTE SIGNATURE + PRIMO/PROXY | 7.4126 | 38% | 0.1072 | 177% | 2.3883 | 57.4% | 0.0225 | 171% |
| PRIMO/PROXY | 5.6425 | 4.8% | 0.067 | 73% | 1.6755 | 10.4% | 0.0187 | 125% |
| ALIETTE SIGNATURE Only | 6.3773 | 18.5% | 0 | — | 1.7953 | 18% | 0 | — |

The turf quality was also rated on a scale of 0 to 9 with a rating of 6 and above considered acceptable. The ratings of the treatments are summarized in Table 4. These data demonstrate that the Poa annua/bentgrass greens treated under an early spring program of a combination of ALIETTE SIGNATURE and PROXY/PRIMO program demonstrate the best turf quality ratings throughout the two month duration of the trial compared to the ALIETTE SIGNATURE or PROXY/PRIMO program alone. All three programs outperformed the untreated plot which essentially was treated with the normal standard program used by the superintendent (see Table 2).

TABLE 4

| | 16-April | 26-April | 4-May | 10-May | 15-May | 30-May | 5-June | 12-June |
|---|---|---|---|---|---|---|---|---|
| PRIMO Only (UTC) | 5.5 | 5.6 | 5.5 | 5.3 | 5.8 | 5.7 | 5.6 | 5.6 |
| PRIMO/PROXY | 5.5 | 5.9 | 6.5 | 5.8 | 6.1 | 6.2 | 7.3 | 7.3 |
| ALIETTE SIGNATURE + PRIMO/PROXY | 5.5 | 6.2 | 7.5 | 7.0 | 7.2 | 7.1 | 8 | 8 |
| Aliette SIGNATURE Only | 5.8 | 5.9 | 6.0 | 6.5 | 6.8 | 6.5 | 7.2 | 7.5 |

The percentage of Poa annua seed head coverage was also measured. These results, as summarized in Table 5, demonstrate that ALIETTE SIGNATURE, when combined with two plant growth regulator compounds, dramatically reduces the number of seed heads.

TABLE 5

| | 15-May | 30-May | 5-June | 12-June |
|---|---|---|---|---|
| PRIMO Only (UTC) | 10 | 20 | 35 | 20 |
| Aliette SIGNATURE + PRIMO/PROXY | 0 | 0 | 3 | 1 |
| PRIMO/PROXY | 0 | 0 | 4 | 1 |
| ALIETTE SIGNATURE Only | 10 | 15 | 35 | 15 |

Trial Location Two

At Location Two, the treatments were applied by a commercial golf course sprayer (spray volume rate 400 L/Ha) as summarized in Table 6. The putting green was a young aggressive Poa annua with seed heads were already showing by 20-April when PROXY/PRIMO was applied. Foliar anthracnose invaded the untreated portion of the green and was heavily infected during the early part of June.

TABLE 6

| Treatment | Amount | Date |
|---|---|---|
| ALIETTE SIGNATURE | 100 g/100 m$^2$ | 16-April |
| PROXY | 159 ml/100 m$^2$ | 20-April |
| PRIMO | 4 ml/100 m$^2$ | 20-April |
| ALIETTE SIGNATURE | 120 g/100 m$^2$ | 17-May |
| PROXY | 159 ml/100 m$^2$ | 8-May |
| PRIMO | 4 ml/100 m$^2$ | 8-May |
| ALIETTE SIGNATURE | 120 g/100 m$^2$ | 14-June |

In addition to the spray treatments set forth in Table 6, cover sprays were applied to the entire trial including the untreated control. These cover sprays are summarized in Table 7.

TABLE 7

| Treatment | Date |
|---|---|
| Fungicide sold under the trademark HERITAGE (watered in for summer patch) | 16-April |
| Fungicide sold under the trademark BANNER MAXX available from Syengenta Crop Protection Inc. of Greensboro, NC | 11-May |
| Fungicide sold under the trademark BANNER MAXX | 2-June |

The turf quality was ated on a scale of 0 to 9 with a rating of 6 and above considered acceptable. The ratings of the treatments are summarized in Table 8.

TABLE 8

| | 16-April | 17-April | 2-May | 15-May | 9-June | 5-June | 12-June |
|---|---|---|---|---|---|---|---|
| PRIMO Only (UTC) | 5 | 5 | 5.5 | 5 | 4 | 5.6 | 5.6 |
| PRIMO/PROXY | 5 | 5 | 6 | 6 | 6.2 | 7.3 | 7.3 |
| ALIETTE SIGNATURE + PRIMO/PROXY | 5 | 5.8 | 6.5 | 6.5 | 7.1 | 8 | 8 |
| ALIETTE SIGNATURE Only | 5 | 5.8 | 6.5 | 5.5 | 6.5 | 7.2 | 7.5 |

The Poa annua/bentgrass greens treated under an early spring program of a combination of ALIETTE SIGNATURE and PROXY/PRIMO program (including core broad spectrum fungicide treatments of HERITAGE, BANNER MAXX and a combination of BANNER MAXX and the fungicide sold under the trademark DACONIL available from Syngenta Crop Protection Inc. of Greensboro, N.C., applied to all treatments including the untreated control (UTC)) consistently showed improved turf color, higher density, overall improved turfgrass health and an improved putting surface with approximately 50-60% seed head control of *Poa annua*. The improvement in color was immediate upon application of ALIETTE SIGNATURE. PROXY/PRIMO alone demonstrated improved color and overall improved putting quality over a time period of three to four weeks. The combination treatments comprising both ALIETTE SIGNATURE and PROXY/PRIMO demonstrated turf quality ratings that were always higher then all other treatments from 17-April to 20-June. Foliar anthracnose did infiltrate trial treatments but was extremely infectious in the untreated control plots.

EXAMPLE 2

Experiments were conducted to determine: (a) the effects of PROXY on carbon allocation and resulting heat stress in both annual bluegrass and creeping bentgrass; and (b) the combined affects of PROXY used in conjunction with ALIETTE SIGNATURE in increasing heat stress in annual bluegrass and creeping bentgrass.

Tillers of Penncross creeping bentgrass and annual bluegrass growing on a sand-based nursery green were brought in from the field and transferred into polyvinylchloride (PVC) tubes 10 cm in diameter and 30 cm in depth filled with sand conforming to United States Golf Association (USGA) specifications. Plants were maintained in a greenhouse at a low height of cut and transferred into a growth chamber for acclimation before the experiment began. Four treatments for each species (eight total) under high temperature (35° day/30° night) were implemented. The treatments for the bentgrass are summarized in Table 9. The treatments for the annual bluegrass are summarized in Table 10. In both cases, PROXY and SIGNATURE were applied in aqueous solutions at a rate of 100 ml/m$^2$.

TABLE 9

| Treatment | Amount |
| --- | --- |
| PROXY | 1.6 ml/m$^2$ |
| SIGNATURE | 1.2 g/m$^2$ |
| PROXY + SIGNATURE | 1.6 ml/m$^2$ + 1.2 g/m$^2$ |
| Water | — |

TABLE 10

| Treatment | Amount |
| --- | --- |
| PROXY | 1.6 ml/m$^2$ |
| SIGNATURE | 1.2 g/m$^2$ |
| PROXY + SIGNATURE | 1.6 ml/m$^2$ + 1.2 g/m$^2$ |
| Water | — |

The experiment began with baseline measurements at the end of the growth chamber acclimation time period of one week. Measurements included a rating of general turf quality and chlorophyll content estimated by canopy reflectance. All treatments were applied twice at a two week interval before heat stress was introduced. In the fifth week, the heat treatment was applied to all treatments. Four days into week three, the day/night temperature in the growth chamber were ramped up from the starting temperatures (20° C. day/15° C. night) until they reached 35° C. day/30° C. night fifteen days later. Throughout the experiment the plants were watered and fertilized to maintain optimum growth under the temperature regime.

Pots were assessed a visual rating based on a scale of 0-10, with 10 being the best rating, for drought/heat stress symptoms and living cover. The results of the visual ratings for the bentgrass are summarized in Table 11. The results of the visual ratings for the bluegrass are summarized in Table 12.

TABLE 11

|  | 25-Jan | 30-Jan | 04-Feb | 07-Feb | 12-Feb | 15-Feb | 21-Feb | 27-Feb | 06-Mar |
| --- | --- | --- | --- | --- | --- | --- | --- | --- | --- |
| PROXY | 10 | 10 | 10 | 10 | 9.8 | 9.7 | 9.2 | 5.7 | 1.8 |
| SIGNATURE + PROXY | 10 | 10 | 10 | 10 | 10 | 9.8 | 9.5 | 6.5 | 0.7 |
| SIGNATURE | 10 | 10 | 10 | 10 | 10 | 9.8 | 9.8 | 8.7 | 3.7 |
| Water | 10 | 10 | 10 | 10 | 10 | 10 | 9.5 | 7.2 | 5.2 |

TABLE 12

|  | 25-Jan | 30-Jan | 04-Feb | 07-Feb | 12-Feb | 15-Feb | 21-Feb | 27-Feb | 06-Mar |
| --- | --- | --- | --- | --- | --- | --- | --- | --- | --- |
| PROXY | 9.4 | 9.4 | 9.6 | 9.8 | 9.4 | 9.2 | 9.2 | 6.6 | 0.6 |
| SIGNATURE + PROXY | 9.5 | 9.7 | 9.8 | 9.8 | 10 | 9.8 | 9.7 | 5.7 | 3.5 |
| SIGNATURE | 9.8 | 9.8 | 9.7 | 9.7 | 9.5 | 9.5 | 9.7 | 5.8 | 1.7 |
| Water | 10 | 10 | 10 | 10 | 9.8 | 9.7 | 9.5 | 7.5 | 3.8 |

Roots harvested at the end of the experiment were dried and weighed. The root systems were divided into the upper 10 centimeters and the lower 20 centimeters. The dry matter weight of the bentgrass treatments (mean of six pots) are summarized in Table 13. The dry matter weight of the bluegrass treatments (mean of six pots) are summarized in Table 14.

TABLE 13

| Treatment | Top 10 cm (mg) | Bottom 20 cm (mg) |
| --- | --- | --- |
| PROXY | 540.4 | 420.5 |
| SIGNATURE + PROXY | 646.1 | 299.1 |
| SIGNATURE | 664.2 | 866.4 |
| Water | 624.2 | 720.3 |

TABLE 14

| Treatment | Top 10 cm (mg) | Bottom 20 cm (mg) |
|---|---|---|
| PROXY | 427.9 | 65.2 |
| SIGNATURE + PROXY | 666.1 | 347.0 |
| SIGNATURE | 675.7 | 286.3 |
| Water | 597.4 | 330.6 |

Both creeping bentgrass and bluegrass treated with PROXY demonstrated a significant decline in canopy reflectance readings. Heat stress increased the decline. SIGNATURE by itself had little effect on either the bluegrass or creeping bentgrass compared to the control. The combined treatment with PROXY and SIGNATURE indicated a safening effect in the bluegrass. The safening of the combined PROXY and SIGNATURE treatments on bluegrass was evident, particularly in the lower 20 cm of the root systems as shown by the root dry matter differences.

EXAMPLE 3

Field trials were conducted to determine the effects of turf quality when either an SC formulation of a colorant formulation of Pigment Green #7 for a liquid variorum or a WG formulation of pigment Green #7 for solid version sold under the trademark STRESSGARD and available from Bayer CropScience LP of Research Triangle Park, N.C. and fosetyl-Al turf fungicide sold under the trademark CHIPCO SIGNATURE available from Bayer CropScience LP of Research Triangle Park, N.C. were individually combined with PROXY and PROXY/PRIMO. Trials were conducted on a pushup green (soil based green) with a mixed stand 60/40 of *Poa annua*/bentgrass. The treatments are summarized in Table 15.

TABLE 15

| Entry | Treatment | Dosage | Dosage Unit | Transformed Dosage | Transformed Dosage Unit |
|---|---|---|---|---|---|
| 1 | Untreated | — | — | — | — |
| 2 | PROXY | 38.2 | GA/100 m² | 5 | oz/1000 ft² |
| 3 | Pigment Green #7 Liquid | 0.121 | ml/m² | 0.38 | oz/1000 ft² |
| 4 | PROXY | 38.2 | GA/100 m² | 5 | oz/1000 ft² |
|   | PRIMO | 0.477 | GA/100 m² | 0.125 | oz/1000 ft² |
| 5 | PROXY | 38.2 | GA/100 m² | 5 | oz/1000 ft² |
|   | Pigment Green #7 Liquid | 0.121 | ml/m² | 0.38 | oz/1000 ft² |
| 6 | PROXY | 38.2 | GA/100 m² | 5 | oz/1000 ft² |
|   | PRIMO | 0.477 | GA/100 m² | 0.125 | oz/1000 ft² |
|   | Pigment Green #7 Liquid | 0.121 | ml/m² | 0.38 | oz/1000 ft² |
| 7 | PROXY | 38.2 | GA/100 m² | 5 | oz/1000 ft² |
|   | PRIMO | 0.477 | GA/100 m² | 0.125 | oz/1000 ft² |
|   | Cyclanilide 2.8% SC | 0.67 | GA/100 m² | 0.49 | oz/gal |
|   | Pigment Green #7 Liquid | 0.121 | ml/m² | 0.38 | oz/1000 ft² |
| 8 | CHIPCO SIGNATURE | 200 | G/100 m² | 6.55 | oz/1000 ft² |
|   | PROXY | 38.2 | GA/100 m² | 5 | oz/1000 ft² |
|   | PRIMO | 0.477 | GA/100 m² | 0.125 | oz/1000 ft² |

All treatments (2-8), except for the untreated control, were applied 19-April based on 200 degree days (base 50° F.). CHIPCO SIGNATURE alone was applied to 8 plots only on 4-May. All treatments (2-8) were then reapplied on 10-May. On 19-June, four root core samples were taken from each plot in the trial. The trial was set up as a randomized complete block design (RCBD) with 4 replicates. The top 4 inches of each sample were combined and bagged separately. The remaining core samples below 4 inches were also combined per treatment and bagged separately. The turf cores were washed and dry root weights were taken for the top 4 inch samples and the below 4 inch samples. Visual turf quality rating 0-10 scale (6=acceptable) and % *Poa annua* seed head expression ratings per plot were measured during the trial.

An average total root weight (grams) of all 8 treatments was calculated. The treatments without Pigment Green #7 (i.e., 1, 2, and 4) demonstrated the lowest total root weights. An average root weight (grams) was also calculated for the top 4 inches of the 8 treatments. The treatments without Pigment Green #7 (i.e., 1, 2, and 4) demonstrated the lowest average root weights in the top 4 inches of the root core samples. Lastly, an average total weight (grams) was calculated for the total root weight below 4 inches of the 8 treatments. Untreated plots and Pigment Green #7 applied alone plots (Treatment 3) demonstrated the highest average total root weight below 4 inches. All treatments containing PROXY showed lower root weights below 4 inches in depth compared to the untreated control and Pigment Green #7 alone treatments. When Pigment Green #7 was added to PROXY (treatment 5) a substantial increase in root mass samples (approximately 50% increase) below 4 inches was achieved compared to PROXY applied alone (treatment 2). Thus, Pigment Green #7, when combined with at least one plant growth regulator, demonstrated the ability to increase root weight Next, the turf quality was rated on a scale of 0 to 10 with a rating of 6 and above considered acceptable. The mean turf quality ratings of the treatments are summarized in Table 16. In summary, Pigment Green #7 was shown to improve turf quality when combined with PROXY or PROXY/PRIMO in this trial as did CHIPCO SIGNATURE.

TABLE 16

|   | Untreated Control | PROXY | PROXY + Pigment Green #7 | PROXY + PRIMO | PROXY + PRIMO + Pigment Green #7 | SIGNATURE + PROXY + PRIMO | Cyclanilide + PROXY + PRIMO + SIGNATURE | Pigment Green #7 |
|---|---|---|---|---|---|---|---|---|
| Mean Turf Quality Rating | 6.12 | 6.0 | 6.68 | 5.98 | 6.94 | 6.7 | 6.94 | 7.16 |

Lastly, the PROXY/PRIMO/Pigment Green #7 and combination treatment of Cycleanilide/PROXY/PRIMO/Pigment Green #7 produced the lowest number of seed heads. The latter treatment demonstrated superior seed head suppression in the trial (98% control) and was statistically significantly different from all other treatments.

EXAMPLE 4

Experiments were conducted to determine the turf quality, color and phytotoxicity of bentgrass when paclobutrazol sold under the trademark TRIMMIT 2SC (available from Syngenta Crop Protection of Greensboro, N.C.) and PRIMO are used alone and in combination with Pigment Green #7. The treatments are summarized in Table 17.

TABLE 17

| Entry | Treatment | Active Ingredient Concentration | Active Ingredient Concentration Unit | Dosage | Dosage Unit |
|---|---|---|---|---|---|
| 1 | Untreated | — | — | — | — |
| 2 | PRIMO | 120 | GA/L | 0.477 | GA/100 m$^2$ |
| 3 | PRIMO | 120 | GA/L | 0.477 | GA/100 m$^2$ |
|   | Pigment Green #7 Liquid | 120 | GA/L | 0.605 | L/HA |
| 4 | PRIMO | 120 | GA/L | 0.955 | GA/100 m$^2$ |
| 5 | PRIMO | 120 | GA/L | 0.955 | GA/100 m$^2$ |
|   | Pigment Green #7 Liquid | 120 | GA/L | 0.605 | L/HA |
| 6 | PRIMO | 120 | GA/L | 0.477 | GA/100 m$^2$ |
|   | Pigment Green #7 Liquid | 120 | GA/L | 1.21 | L/HA |
| 7 | PRIMO | 120 | GA/L | 0.955 | GA/100 m$^2$ |
|   | Pigment Green #7 Liquid | 120 | GA/L | 1.21 | L/HA |
| 8 | TRIMMIT 2SC Paclobutrazol | 250 | GA/L | 1.17 | L/HA |
|   |  | 250 | GA/L | 293 | G |
| 9 | TRIMMIT 2SC Paclobutrazol | 250 | GA/L | 1.17 | L/HA |
|   |  | 250 | GA/L | 293 | g |
|   | Pigment Green #7 Liquid | 120 | GA/L | 0.605 | L/HA |
| 10 | TRIMMIT 2SC Paclobutrazol | 250 | GA/L | 1.17 | L/HA |
|   |  | 250 | GA/L | 293 | g |
|   | Pigment Green #7 Liquid | 120 | GA/L | 1.21 | L/HA |

The turf quality was rated on a scale of 1 to 9. The turf quality ratings of the treatments are summarized in Table 18. Plots treated with Pigment Green #7 were shown to improve turf quality when combined with PRIMO or paclobutrazol.

TABLE 18

| Entry | Treatment | Turf Quality Rating 24-Oct | Turf Quality Rating 13-Nov |
|---|---|---|---|
| 1 | Untreated | 6.0 | 6.0 |
| 2 | PRIMO | 7.0 | 7.2 |
| 3 | PRIMO Pigment Green #7 Liquid | 7.5 | 7.5 |
| 4 | PRIMO | 6.3 | 7.5 |
| 5 | PRIMO Pigment Green #7 Liquid | 7.5 | 7.5 |
| 6 | PRIMO Pigment Green #7 Liquid | 7.7 | 7.3 |
| 7 | PRIMO Pigment Green #7 Liquid | 8.2 | 8.3 |
| 8 | TRIMMIT 2SC Paclobutrazol | 4.7 | 6.2 |
| 9 | TRIMMIT 2SC Paclobutrazol Pigment Green #7 Liquid | 6.0 | 6.2 |
| 10 | TRIMMIT 2SC Paclobutrazol Pigment Green #7 Liquid | 7.3 | 7.5 |

Next, the phytotoxicity (phygen) was rated. The results are summarized in Table 19. The plots treated with Pigment Green #7 exhibited lower phygen ratings compared to those plots that were treated with only a plant growth regulating compound. Also, plots treated with a higher application rate (L/Ha) of Pigment Green #7 exhibited improved phytotoxicity over those plots receiving the same plant growth regulator with a lower application rate of Pigment Green #7.

TABLE 19

| Entry | Treatment | Phygen 5-Oct | Phygen 24-Oct |
|---|---|---|---|
| 1 | Untreated | 0.0 | 0.0 |
| 2 | PRIMO | 6.7 | 3.3 |
| 3 | PRIMO Pigment Green #7 Liquid | 0.0 | 0.0 |
| 4 | PRIMO | 15.0 | 11.7 |
| 5 | PRIMO Pigment Green #7 Liquid | 1.7 | 0.0 |
| 6 | PRIMO Pigment Green #7 Liquid | 0.0 | 0.0 |
| 7 | PRIMO Pigment Green #7 Liquid | 0.0 | 0.0 |
| 8 | TRIMMIT 2SC Paclobutrazol | 18.3 | 26.7 |
| 9 | TRIMMIT 2SC Paclobutrazol Pigment Green #7 Liquid | 3.3 | 10.0 |
| 10 | TRIMMIT 2SC Paclobutrazol Pigment Green #7 Liquid | 0.0 | 3.3 |

The turf color was rated on a scale of 1 to 9. The color ratings of the treatments are summarized in Table 20. Plots treated with Pigment Green #7 were shown to improve turf color when combined with PRIMO. Plots treated with paclobutrazol exhibited improved turf color over those plots treated with PRIMO as well as those treated with PRIMO and Pigment Green #7.

TABLE 20

| Entry | Treatment | Color 13-Nov |
|---|---|---|
| 1 | Untreated | 5.3 |
| 2 | PRIMO | 6.7 |
| 3 | PRIMO Pigment Green #7 Liquid | 7.0 |
| 4 | PRIMO | 6.8 |
| 5 | PRIMO Pigment Green #7 Liquid | 6.8 |
| 6 | PRIMO Pigment Green #7 Liquid | 6.8 |
| 7 | PRIMO Pigment Green #7 Liquid | 7.3 |
| 8 | TRIMMIT 2SC Paclobutrazol | 8.0 |
| 9 | TRIMMIT 2SC Paclobutrazol Pigment Green #7 Liquid | 8.0 |
| 10 | TRIMMIT 2SC Paclobutrazol Pigment Green #7 Liquid | 8.0 |

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. An agricultural combination for enhancing turf comprising:
   (a) at least one plant growth regulator comprising ethephon, trinexapac ethyl, paclobutrazole, flurprimidol or a combination thereof; and
   (b) at least one pigment comprising a phthalocyanine compound; and
   at least one fungicide comprising fosetyl aluminum,
   wherein the combination provides phytoregulation and reduced phytotoxicity as compared to an equivalent application of the plant growth regulator alone in turf.

2. The agricultural combination of claim 1, wherein the at least one plant growth regulator is a combination of ethephon and trinexapac ethyl.

3. The agricultural combination of claim 1, wherein the at least one fungicide further comprises, trifloxystrobin, triadimefon, triticonazole, iprodione or a combination thereof.

4. The agricultural combination of claim 1, wherein the phthalocyanine compound is Pigment Blue 16, Vat Blue 29, Pigment Blue 15, Heliogen Green GG, Ingrain Blue 14, Ingrain Blue 5, Ingrain Blue 1, Pigment Green 37, Pigment Green 7, or a combination thereof.

5. The agricultural combination of claim 1, wherein said pigment is present in an amount of between about 1 to about 900 parts by weight of total composition.

6. The agricultural combination of claim 1, wherein the combination is an aqueous suspension or a wettable powder.

7. A method for enhancing turf quality comprising applying an effective amount of a combination according to claim 1 to the turf.

8. The method of claim 7, wherein said at least one pigment is present in an approximate amount of about 1 to about 900 parts by weight of the total composition.

9. The method of claim 7, wherein said combination is applied in an amount of from about 300 to about 800 L/ha.

10. The method of claim 7, wherein said combination is applied to the turf selected from Bluegrass, Bentgrass, Fescue, Ryegrass, Wheatgrass, Beachgrass, Orchardgrass, Timothy, Smooth Brome, Bermudagrass, Zoysiagrass, St. Augustinegrass, Centipedegrass, Carpetgrass, Bahiagrass, Kikuyugrass, Buffalograss, Blue Grama, and Sideoats Grama.

11. The method of claim 10, wherein the turf is said Bluegrass, Bentgrass, Fescue, or Ryegrass.

12. A system for turf management comprising a combination according to claim 1.

13. The agricultural combination of claim 1, wherein said phthalocyanine compound comprises copper.

14. The agricultural combination of claim 1, wherein said fungicide consists essentially of fosetyl aluminum.

15. The agricultural combination of claim 1, wherein said at least one plant growth regulator comprises ethephon.

16. The agricultural combination of claim 1, wherein said at least one plant growth regulator comprises trinexapac ethyl.

17. The agricultural combination of claim 1, wherein said at least one plant growth regulator comprises paclobutrazole.

18. The agricultural combination of claim 1, wherein said at least one plant growth regulator comprises flurprimidol.

19. The agricultural combination of claim 1, wherein said at least one plant growth regulator comprises ethephon, and wherein said fungicide consists essentially of fosetyl aluminum.

20. The agricultural combination of claim 1, wherein said at least one plant growth regulator comprises trinexpac ethyl, and wherein said fungicide consists essentially of fosetyl aluminum.

21. The method of claim 7, wherein said at least one plant growth regulator and said at least one pigment and said at least one fungicide are applied sequentially.

22. The method of claim 7, wherein said at least one plant growth regulator and said at least one pigment and said at least one fungicide are applied simultaneously.

23. An agricultural combination comprising:
   (a) at least one plant growth regulator comprising ethephon, trinexapac ethyl, paclobutrazole, flurprimidol or a combination thereof;
   (b) phthalocyanine; and
   at least one fungicide comprising fosetyl aluminum,
   wherein the at least one plant growth regulator retards growth or reduces the number of seed heads in turf.

* * * * *